United States Patent [19]

Riley et al.

[11] Patent Number: 4,692,308

[45] Date of Patent: Sep. 8, 1987

[54] AUTOMATIC CHEMICAL ANALYSIS

[75] Inventors: Clifford Riley, Burgess Hill; Christopher J. Mears, Guilford, both of United Kingdom

[73] Assignee: Vickers, PLC, London, England

[21] Appl. No.: 827,151

[22] Filed: Feb. 7, 1986

Related U.S. Application Data

[63] Continuation of Ser. No. 525,818, Aug. 23, 1983, abandoned, which is a continuation-in-part of Ser. No. 493,382, Mar. 17, 1983, abandoned.

[30] Foreign Application Priority Data

Mar. 17, 1982 [GB] United Kingdom ............... 8207814

[51] Int. Cl.$^1$ ........................................... G01N 35/04
[52] U.S. Cl. ........................................ 422/65; 422/63; 422/81; 422/82; 422/100; 436/43; 436/52; 436/53
[58] Field of Search ............................ 422/63-65, 422/67, 81, 82, 100; 436/52, 53, 43

[56] References Cited

U.S. PATENT DOCUMENTS

| | | | |
|---|---|---|---|
| 3,230,776 | 1/1966 | Isreeli et al. | 422/64 |
| 3,418,053 | 12/1968 | Pelavin | 422/82 |
| 3,567,393 | 3/1971 | Welch | 422/64 |
| 3,764,268 | 10/1973 | Kosowsky et al. | 422/82 |
| 3,804,593 | 4/1974 | Smythe et al. | 422/82 |
| 3,985,508 | 10/1976 | Williams | 422/65 |
| 4,039,286 | 8/1977 | Keller et al. | 422/67 |
| 4,058,367 | 11/1977 | Gilford | 422/67 |
| 4,113,436 | 9/1978 | Werder et al. | 422/65 |
| 4,170,625 | 10/1979 | Welch | 422/64 |
| 4,338,279 | 7/1982 | Orimo et al. | 422/65 |
| 4,447,395 | 5/1984 | Englar et al. | 422/63 |
| 4,456,580 | 6/1984 | Yamada et al. | 422/63 |
| 4,483,927 | 11/1984 | Takekawa | 422/67 |

FOREIGN PATENT DOCUMENTS 58-26270 2/1983 Japan ................................. 422/65

Primary Examiner—Michael S. Marcus
Attorney, Agent, or Firm—Wegner & Bretschneider

[57] ABSTRACT

Apparatus for, and a method of, automatic chemical analysis. The apparatus comprises a conveyor system for delivering vials containing samples for analysis through an entry gate and identification arrangement to a series of analytical modules where a succession of tests is effected on each of the samples. Each of the analytical modules comprises a sample probe, a reagent probe, a container for reagent adjacent to the conveyor means, a movable stop member arranged to hold a vial in an appropriate position adjacent to the module, means for moving the movable stop member so as to allow the vial to pass from one module to the next, and means for moving the sample and reagent probes between a first position where they are ready for insertion into a vial, and a second position where they are held clear of the vial. The apparatus also includes synchronizing means arranged to co-ordinate operation of the various elements of the apparatus.

In the method, the vials pass sequentially through the entry gate of the above apparatus at a predetermined rate, and a portion of each of the samples is extracted while the vial is at an analysis station adjacent to one of the analytical modules. A portion of reagent is simultaneously extracted and is combined with the extracted sample into a single flow line. The combined reagent-/sample is subjected to an analytical test within the module.

14 Claims, 10 Drawing Figures

AUTOMATIC CHEMICAL ANALYSIS

This application is a continuation of Ser. No. 525,818, filed Aug. 23, 1983, abandoned, which is a continuation-in-part of Ser. No. 493,382, filed Mar. 17, 1983, abandoned.

BACKGROUND OF THE INVENTION

This invention relates to automatic chemical analysis and more particularly, but not exclusively, is concerned with apparatus including modular units for carrying out chemical analyses automatically.

Various types of analytical apparatus are known. One type of apparatus is known as a discrete analyser, and in this apparatus a sample is placed in an individual container where, in general, it remains for the duration of the analytical procedure which is carried out. An advantage of this arrangement is that each discrete sample can be individually labelled, so that confusion between different samples is minimised.

In a further type of apparatus, samples travel continuously, or quasi-continuously, in a carrier stream moving along a narrow flow channel which is designed so that each individual sample retains its integrity with respect to adjacent samples. In certain previous systems, slugs of air have been used to separate individual samples in the moving stream. In other systems, the carrier medium is the reagent with which the individual samples are to react.

European Patent Specification No. 0047130 describes a method of analysis of a liquid sample which is carried along a flow channel by a carrier liquid, which method comprises simultaneously extracting by aspiration from separate containers a predetermined quantity of a given sample and a predetermined quantity of a selected reagent therefor; bringing the extracted sample and the extracted reagent together; and causing the sample/reagent mixture to travel along said flow channel as a discrete liquid slug interposed in the stream of carrier liquid to the measurement cell of an analytical instrument. This method can be used in the sequential analysis of a series of samples, and can operate either with a plurality of samples simultaneously present at different positions within the flow channel, or with just a single sample in the flow channel at any one time. Also, the method of European Patent Specification No. 0047130 does not involve the use of air bubbles to segment the carrier liquid. Thus the material present in the flow channel is in the form of a continuous liquid, the carrier liquid having interposed therein discrete liquid slugs of sample/reagent mixture, which can conveniently be termed "active slugs". Conveniently in this method, the carrier liquid is deionized water.

The present invention is concerned with analysis apparatus which can be used to carry out the method described in European Patent Specification No. 0047130. The apparatus of the present invention, however, is not limited to such use; other analytical procedures can equally well be carried out using the apparatus of this invention.

SUMMARY OF THE INVENTION

According to one aspect of the present invention, there is provided an automatic analysis apparatus, which comprises conveyor means for delivering vials containing samples for analysis to a first position; an entry gate located at said first position for admitting vials sequentially at a predetermined rate; identification means adjacent to said entry gate for reading a sample identifying code carried by each of the vials; synchronising means; and a plurality of analytical modules positioned downstream of the entry gate, wherein each of the analytical modules comprises:

(a) a sample probe for insertion into a vial for extracting a portion of the sample therein.

(b) a reagent container adjacent to the conveyor means, (c) a reagent probe for extracting a quantity of reagent from the reagent container, (d) a movable stop member arranged to hold a vial on the conveyor means in a holding position where the sample probe can enter the vial for sample extraction, (e) means for moving the movable stop member from the holding position to a further position where the vial is free to be moved by the conveyor means to the next analytical module, and (f) means for moving the sample and reagent probes between a first operative position, where they are positioned for insertion into, respectively, a vial held at the said holding position and a reagent container, and a second operative position where the sample probe is positioned so as to be clear of the vial; and wherein the synchronising means is arranged to coordinate the operation of the entry gate, the identification means, the probe moving means and the means for moving the movable stop member of each of the analytical modules.

Preferably, each of the analytical modules also includes means for supplying a reagent to its reagent container. It is also preferred for each analytical module to be associated with a container for a carrier liquid, for example deionised water, into which the sample probe can be located when in the said second operative position. Preferably, the reagent probe is moved (as well as the sample probe) from the first operative position to a second operative position; in the latter, the reagent probe will be positioned so as to be clear of the reagent container and more preferably it will be located in the same container for carrier liquid as is the sample probe. Conveniently, the sample and reagent probes can be carried by a common arm. Generally, such an arm will be positioned above the location of the movable stop member.

According to another aspect of the present invention, there is provided a method of carrying out a plurality of analytical tests on each of a plurality of samples, which comprises feeding vials containing the samples in succession to an entry gate; allowing the vials to pass through said entry gate sequentially and at a predetermined rate; conveying each of the samples in turn to a series of analytical modules placed side-by-side; extracting a portion of each sample while it is at an analysis station adjacent to a given one of the analytical modules and simultaneously extracting a quantity of a reagent for use in the analysis of the sample; combining the extracted sample and the extracted reagent into a single flow line; subjecting the combined reagent/sample to an analytical test within the said analytical module; thereafter causing the vial to move to the next analysis station for a further analytical test while the next vial is moved to the first-mentioned analysis station; and repeating the sequential movement of vials until the samples within each of the vials has undergone an analytical test at each of the analysis stations.

DESCRIPTION OF THE PREFERRED EMBODIMENTS

Preferably, the reagent and sample are brought together into a common flow line within the analytical module after their extraction. A carrier liquid is preferably caused to enter the common flow line upstream of the reagent/sample mixture, and the fluid within the flow line is supplied to an analytical instrument, e.g. a spectrophotometer. After the reagent/sample mixture has been analysed, material in the said flow line can be evacuated to waste. Preferably the samples are contained in vials which carry individual bar code labels. The vials are advantageously caused to travel in a generally linear path from the entry gate through the series of analysis stations.

In one embodiment of the apparatus of the invention, the sample and reagent probes are held by an arm which is secured to a hollow, movable shaft having a disc at its base. The hollow shaft is fitted loosely over a fixed vertical rod. The disc at the base of the shaft is formed with a radial slot which is positioned to cooperate with a cam rotatable about a generally horizontal axis and positioned beneath the disc. A pin is provided on or near the circumference of the cam, the arrangement being such that rotation of the cam causes the cam surface first to contact the basal disc, thereby pushing the disc and the hollow shaft to which it is attached upwardly. This in turn causes the arm carrying the reagent and sample probes to be lifted with respect to the apparatus as a whole. Further rotation of the cam causes its pin to enter the radial slot formed in the basal disc, and to exert a pulling action thus causing the disc and the structures supported thereby to rotate about the fixed vertical rod. This results in the sample and reagent probes being swung about the axis defined by the fixed vertical rod. Further rotation of the cam enables the pin to become free of the radial slot, so that no further rotation of the disc occurs. The cam is profiled so that, after the disc has been rotated to the fullest extent allowed by the geometry of the arrangement, further rotation of the cam causes the disc and the parts which it carries to be lowered until the arm carrying the sample and reagent probes once more resets atop the fixed vertical rod. It will be appreciated that the movement of the probe-carrying arm in the manner just described suffices to move the probes from their first operative position to their second operative position. It is only necessary to ensure that the probe-carrying arm is lifted and rotated through a relatively small range in order to effect the movement of the probes between the operative and inoperative positions. Generally, a rotation within the range 20° to 75° will suffice. Advantageously, the basal disc attached to the hollow, movable shaft is provided with a stop member which co-operates with a suitably positioned surface to prevent overshoot of the disc in the course of its rotational movement. The cam which effects movement of the basal disc is preferably driven by a stepping motor. This enables accurate control of the movement. Conveniently, the probe-carrying arm has the sample probe at its outer end (i.e. remote from the hollow, movable shaft) and has the reagent probe positioned inwardly thereof (i.e. closer to the hollow-movable shaft). With this construction, the sample probe can enter a vial which is held in position on the conveying means while the reagent probe enters the reagent container located between the conveyor means and the body of the analysis module and whose position can be fixed with respect to the rest of the analysis module. When the cam rotates to effect movement of the probes away from their first operative position, the probes are initially lifted upwardly out of the vial and reagent container, respectively, and are then rotated while in the raised condition before being lowered to a second operative position away from the reagent container and vial, respectively. In this second position, both of the probes can dip into a container of carrier liquid, e.g. deionised water. It will be appreciated that rotation of the cam in the reverse direction serves to reverse the sequence of movements of the probes. As just described, the probe-carrying arm has only one reagent probe. The arm, however, may carry more than one reagent probe, in which case the reagent probes will each have associated therewith a separate reagent container, and the reagent probes will be positioned on the probe-carrying arm accordingly.

The cam which co-operates with the basal disc in the manner described above can also be used directly or indirectly as the means for moving the movable stop member from the holding position (in which it holds a vial on the conveyor means so that the sample probe can enter the vial) to the further position where the vial is free to be moved by the conveyor means to the next analytical module. It will be appreciated that the movable stop member, when in the holding position, cooperates with the conveyor means carrying a sample for analysis to define an analytical station; movement of the stop member thus allows the sample to travel from one analysis station to the next while supported by the conveyor means. The conveyor means may be driven continuously or intermittently (i.e. only when transfer of the vials from one analytical station to the next is required). The movable stop member acts as a bar across the line of movement of the conveyor means when in the holding position, the stop member being withdrawn (e.g. by being rotated about a generally vertical axis) from the holding position, thus allowing the conveyor to carry the vial downstream.

Preferably, the conveyor means comprises at least one endless belt conveyor which conveys the vials to the first position where they are held by the entry gate for sequential admission to the analysis stations. A preferred arrangement comprises a pair of endless conveyor belts placed side-by-side and arranged to run in opposite directions. The belts are adjacent to the analytical modules, that one of the two belts more remote from the module being the one onto which the vials are intially placed. A curved guide is located at or near one end of the belts and is positioned across the belts so that vials travelling along the outer of the two belts are urged, by the curved guide, to transfer across a relatively narrow intermediate supporting surface to the other of the two endless conveyors. To assist in this transfer motion, the zone between the two endless belts preferably includes an upstanding wall which is positioned to make a highly acute angle with the direction of movement of the outer of the two belts and which has a wedge-shaped cross-section at the end thereof nearest to the curved guide. We have found that such an obliquely positioned wall assists in transferring the vials (which are generally cylindrical in form) from one belt to the other. Conveniently, a single motor can be used to drive both of the belts.

The entry gate is preferably in the form of a retractable and/or rotatable member which can be interposed across the direction of travel of the vials as they approach the analytical modules. In a preferred embodiment, the entry gate comprises a generally horizontal wheel which acts as a cam follower and which is urged against the surface of a generally horizontal cam, the cam having a radius substantially larger than that of the wheel. The profile of the cam is circular except for an indented region. When the wheel is in contact with the major, circular portion of the circumference of the cam, it obstructs passage along the adjacent conveyor belt, and thus prevents access of the vials to the analysis stations. As the wheel enters the indented region of the cam's circumference, it moves away from the conveyor belt, thus allowing a vial to pass towards the first of the analytical modules. In order to ensure that only a single vial passes through the entry gate at a time, there is preferably a second retractable member arranged upstream of the wheel. This member can be, for example, a lever which can also act as a cam follower. For this purpose, a second cam may be carried on the same axis as the cam just described, and positioned beneath that cam. The lever is urged against the lower cam, and the lever, the profile of the lower cam and its orientation with respect to the upper cam are such that the lever moves away from the conveyor belt shortly after the biased wheel has come out of the indented area of the upper cam, the first vial having been moved towards the first analysis station. The upper cam thus leads with respect to the lower cam, and the overall effect is that the lever holds back subsequent vials while the first is at the entry gate, and until the first vial has passed through the gate; once the biased wheel has returned to obstruct the conveyor pathway, the lever allows the next vial to enter the gate. When this vial has passed the lever, it moves up against the biased wheel; the lever itself then moves to obstruct the pathway along the conveyor, thereby retaining subsequent vials at the waiting position.

Conveniently, an entry gate of the type just described can be used in conjunction with an identification unit (for example a light pen) to read an identification label (e.g. a bar code label) attached to each of the vials. This can be achieved by covering the perimeter of the biased wheel with a friction material such as a rubber ring. Once a given vial is positioned between the biased wheel and the lever, the rotation of the wheel in contact with the upper cam's surface causes the vial to rotate, so that a light pen positioned adjacent to the entry gate can read the identification label provided on the vial. In order to ensure that the identification code is read in full, regardless of the orientation of the vial as it enters the entry gate, it is preferred that the biased wheel effects at least three rotations of the vial before the wheel is withdrawn from the conveyor pathway to allow the vial to move onwards. It is similarly preferred that the cam which drives the biased wheel should rotate exactly once in the course of admitting each vial through the entry gate.

The synchronising means is advantageously a microprocessor which is used inter alia to drive stepping motors which actuate movement of the reagent and sample probes and of the movable stop member, and operation of the peristaltic pump and of the entry gate. If the identification means itself moves in the course of operation of the apparatus, the synchronising means may also control such movement. Likewise, if the conveyor means is driven intermittently, the synchronising means may control the conveyor drive.

After the vials have passed through each of the analysis stations, they are allowed to travel along the conveyor means to a point where they can be collected. Conveniently, the vials are guided onto a collection tray, A detector is preferably provided to ensure that the exit position from the conveyor means is not blocked. The detector means can conveniently be a light beam which is directed across the path of the conveyor means at a position sufficiently far ahead (i.e. downstream) of the last of the analysis stations to ensure that, if a blockage does occur as indicated by the beam being continuously obstructed, there is no risk of the blockage extending far enough upstream to interfere with the operation of any of the analytical modules. This can be achieved using a circuit which measures the length of time during which the light beam is obstructed; if the time period exceeds a predetermined maximum value, the circuit is arranged to cut off the drive to the conveyor means (preferably when the probes are at their second operative position) and thus to initiate shut-down of the analytical system.

Each of the analytical modules is preferably mounted on a fluid-resistant tray supported by a main framework. The analytical equipment within each of the modules is preferably of the type described in European Patent Specification No. 0047130. Preferably, each of the modules has an internal cooling system which may be served by a common cooling duct provided on the lower part of the main framework which holds the analytical modules in position.

The flow channel for the sample/reagent mixture within each of the modules preferably includes a length of nickel tubing which is coiled over a heater and which has a length of about 2 or 3 meters. The heater is preferably controlled thermostatically to an accuracy of within ±0.1° C. Downstream of this heated coil, the nickel tube is adapted to convey its contents to an analytical measuring device. This may be a spectrophotometer, and the nickel tube may be joined to a plastic tube which conveys the sample/reagent mixture through the cuvette of the spectrophotometer. It is preferred to employ two stepping motors within each of the analytical modules, one of the stepping motors driving the peristaltic pump which conveys fluid along the flow channel, and the other stepping motor driving the means for moving the sample and reagent probes and for moving the movable stop member. The peristaltic pump which acts on the fluid within the flow channel may also be used to pump fresh reagent and deionised water into the receptacles adjacent to the conveyor means. Preferably, such provision of the reagent and water is effected continuously so that there is continuous overflow of reagent and water, thus ensuring that there are no losses by evaporation, and no crystallisation, from the reagent.

The vials are preferably placed into support cups before being admitted to the conveyor means. The support cup can include an indented region close to its base so that retaining rails positioned aside the endless belt conveyor can engage with the indented region to hold the support cup firmly in position on the conveyor belt. Such a structure also enables the support cups and vials to be carried by a simple loading tray which includes a scalloped plate which is shaped so as to engage the indented regions of a plurality of support cups.

By arranging an appropriate number of analytical modules side-by-side, an apparatus in accordance with the present invention enables a series of different analytical tests to be carried out on each of a series of samples. The apparatus is expected to find particular application in clinical analysis.

For a better understanding of the invention, and to show how the same may be carried into effect, reference will now be made, by way of example, to the accompanying drawings, in which.

Figure 1:
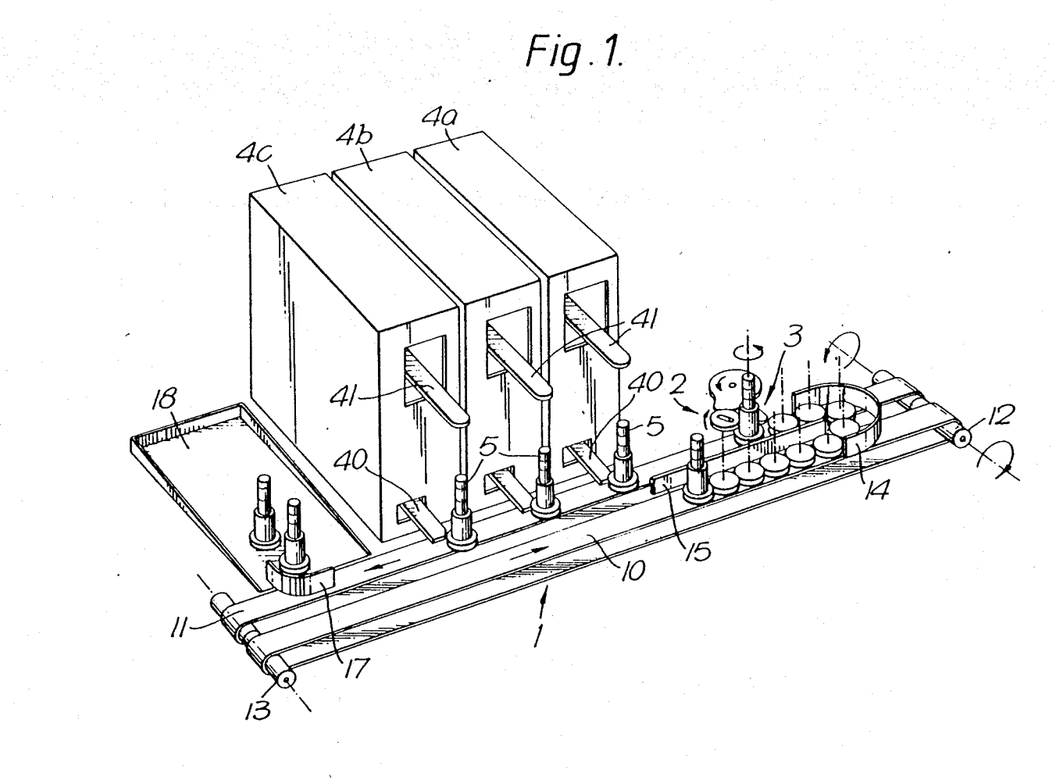
FIG. 1 shows an isometric view of part of an apparatus in accordance with the invention, showing in particular the layout of the conveyor means in relation to the analytical modules.
Figure 8:
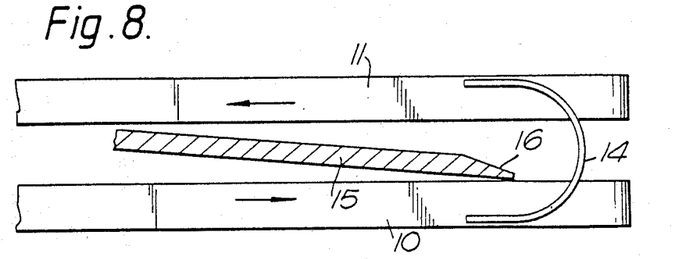
FIG. 8 is a schematic plan view of part of the conveyor means of the apparatus and is not to scale.

Referring now to the drawings, the automatic analysis apparatus comprises a conveyor system 1, an entry gate 2, a bar code reading device shown schematically at 3, and six analytical modules 4a to 4f. For ease of illustration, only three of the modules are shown in FIG. 1. There may of course be more than six analytical modules if desired. The conveyor system includes an outer belt 10 and an inner belt 11 the ends of which are supported on common axles 12 and 13. Each of the belts is 20 mm in width. A single motor can be used to drive one of the axles 12 and 13, and gearing will then be provided to achieve the desired drive directions of belts 10 and 11. As shown in FIG. 1, the outer belt 10 is driven by axles 12 and 13 rotating in a clockwise direction, so that the upper run of the belt moves from left to right; and inner belt 11 is driven in the reverse sense. An upright, curved guide 14 is held in a stationary position close to the right-hand end of the two endless belt conveyors 10 and 11. An upright bar 15 is positioned between the belts 10 and 11, and the right-hand end thereof as seen in the drawings is arranged in the oblique orientation shown more clearly in FIG. 8. The extreme right-hand end of bar 15 is wedge-shaped as shown at 16 and is about one millimeter wide at its end. The gap between end 16 and the nearer edge of conveyor 11 is about eight millimeters in this embodiment. An exit guide 17 is provided close to the left-hand end of belt 11 adjacent to a collection tray 18. As can be seen from FIG. 2, the exit guide 17 may be formed as a continuation of the left-hand end of bar 15. The conveyor system 1 serves to convey vials 5 along the outer belt 10 up to curved guide 14, which co-operates with the wedge-shaped end 16 of central bar 15 to transfer the vials from the outer belt to inner belt 11. The vials are allowed through entry gate 2 which is adjacent to belt 11 at a predetermined rate, and thence travel along belt 11 towards the modules 4a, 4b, etc. After passing through each station in turn, the vials are transferred from belt 11 to collection tray 18 by the action of curved exit guide 17.

Figure 3:
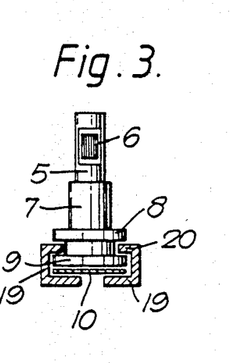
FIG. 3 is a schematic sectional view through part, of the conveyor means of the apparatus with a vial supported thereon.

As shown more clearly in FIG. 3, each vial 5 has a bar code label 6 applied to the upper part thereof. During its travel through the apparatus, each vial 5 is held in a support cup 7 which is carried along by the conveyor system 1. FIG. 3 also illustrates part of the conveyor system which has been omitted from FIG. 1 for reasons of clarity, namely the provision of retaining rails 19 which are positioned on either side of outer belt 10 at least over the downstream portion of the belt (i.e. that part near to the curved guide 14) and preferably over the entire length of the belt except in a region close to the left-hand end of the belt as seen in FIG. 1, at which region the support cups each containing a vial 5 are loaded onto the belt. At this position, a simple guard rail (not shown) is positioned against the outer edge of belt 10. The bar 15 can be arranged so that it has lower flanges which act as rails 19 by co-operating with the inner edge of belt 10 and the outer edge of belt 11. The lower part of each support cup includes an upper flange 8 and a lower flange 9. These flanges are shaped and positioned so as to co-operate with inwardly projecting lips 20 formed at the upper part of the retaining rails 19. The overall height of support cup 7 is such as, to leave bar code label 8 readily visible.

Figure 4:
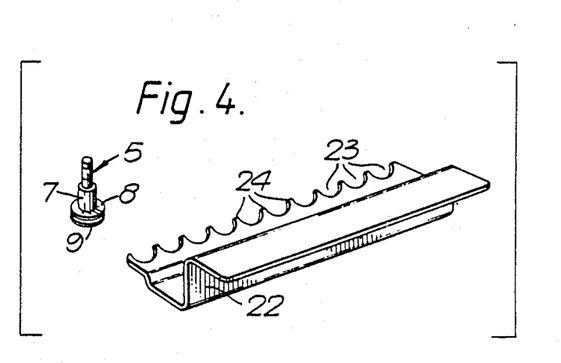
FIG. 4 illustrates a carrying/loading tray which may be used to supply vials to the apparatus.

The use of a support cup having an indented region between flanges 8 and 9 makes it a simple matter to load a plurality of sample-containing vials onto belt 10. For this purpose, a carrying/loading tray 21 having the form shown in FIG. 4 may be used. The functional side of the tray includes a plurality of recesses 22 arranged side-by-side in a scalloped pattern and shaped to fit into the indented region between flanges 8 and 9 of a support cup 7. The projections 23 between adjacent recesses 22 are sufficiently wide to support two adjacent cups 7 securely. In order to load a series of support cups and sample vials onto belt 10, the carrying tray 21 is placed adjacent to the left-hand part of belt 10, i.e. the area where there is a simple guard rail, and is lowered so that the support cups each carrying a sample vial 5 are transferred smoothly onto the upper run of belt 10. The central bar 15 ensures that the support cups do not travel too far transversely of the belt 10 during a loading operation. The drive to belt 10 will then carry the support cups with their vials to the right as seen in FIGS. 1 and 2 towards the curved guide 14 which will assist in their transfer from belt 10 to belt 11.

After the support cups have travelled around guide 14, they queue at entry gate 2 for admission to the down-stream part of belt 11, where the sample analysis is initiated at the analysis stations adjacent to each of the analytical modules.

After each vial has come through the entry gate 2 (the construction and operation of which will be described in greater detail hereafter with reference to FIGS. 9 and 10), it moves towards the first analytical module 4a. As shown in FIG. 1, the vials 5 are held in a stationary position by means of movable stop members 40. A probe-carrying arm 41 extends forwardly of the main body of the analytical module so that its forward extremity is positioned directly above the vial 5. Arm 41 carries a sample probe 47 and a reagent probe 48 (see FIG. 8). Each of the probes is connected to a narrow bore plastics tube 51. A guard rail 21 extends along the length of the inner belt 11 between the belt itself and the analytical modules 4 (see FIG. 2).

Figure 2:
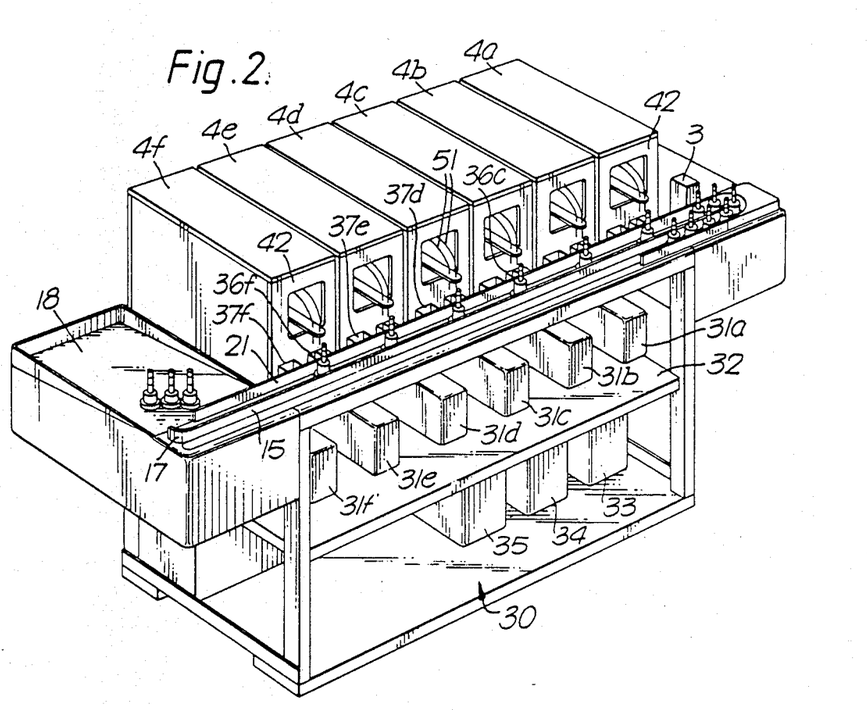
FIG. 2 is a view of the apparatus showing six analytical modules together with some parts of the apparatus not visible in FIG. 1.

FIG. 2 shows the six analytical modules 4a to 4f. Each of the modules is seated on an individual rubber tray (not shown), the trays in turn being supported by the top plate of a housing 30. The housing 30 contains reagent tanks 31a to 31f positioned on a support plate 32 and tanks 33, 34 and 35 located below the support plate 32. Tank 33 holds deionised water, while tanks 34 and 35 are waste containers. Each of reagent tanks 31a to 31f supplies an upwardly extending receptacle 36a to 36f which terminates at a position between guide rail 21 and the front faces 42 of the analytical modules. The water tank 33 similarly supplies a plurality of upwardly extending receptacles 37a to 37f which are positioned adjacent to the reagent receptacles 36a to 36f. The arm 41 and its probes are arranged so that in a first operative position the sample probe 47 is emplaced into a vial 5 held by stop member 40 at an analysis station while reagent probe 48 extends into the appropriate reagent receptacle 36; and in a second operative position both probes 47 and 48 are emplaced in the appropriate water receptacle 37.

Figure 5:
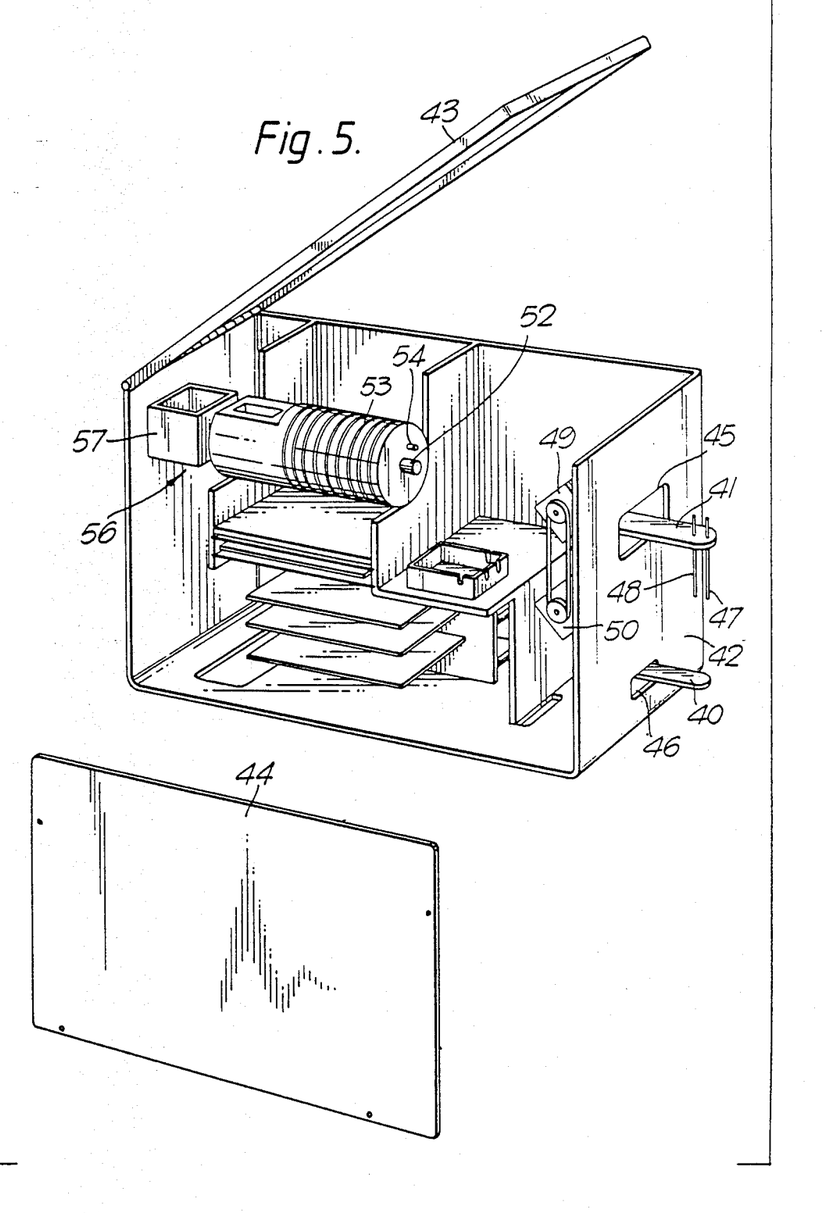
FIG. 5 is a schematic view of the interior of one of the analytical modules.

The construction of each of the analytical modules is shown in FIG. 5. Each module is generally parallel-epipedic in form, and has a front face 42, a hinged top cover 43 and a removable side cover 44. The probe-carrying arm 41 extends through an upper aperture 45 in front face 42, and the movable stop member 40 extends through a lower aperture 46 in front face 42. Sample probe 47 extends from a position close to the forward end of arm 41 and reagent probe 48 is positioned slightly behind the sample probe 47. A peristaltic pump 49 is mounted behind front face 42 and is driven by a pump motor 60 which is a stepping motor under the control of a microprocessor (not shown). The peristaltic pump 49 serves to draw fluid through the probes 47 and 48. Each of the probes 47 and 48 is connected to the narrow bore plastics tubing 51 (see FIG. 2) which extends back through the aperture 45 into the interior of the body of the analytical module. The tubing 51 passes over the rollers of peristaltic pump 49, downstream of which the two tubes 51 are joined together at a Y-piece (not shown). The common outlet from the Y-piece is in the form of a narrow bore nickel tube 3 meters long which is coiled around a heater 52. The coils of nickel tubing are shown at 53. Peristaltic pump 49 is also used to pump fresh reagent and deionised water into the receptacles 36 and 37 adjacent to conveyor 11; pump tubes which connect the respective tanks and receptacles pass over the drive head of the peristaltic pump for this purpose. This pumping operation is effected simultaneously with the pumping of fluids along tubes 51 and 53. It is preferred for the reagent and water supply to be quasi-continuous, since this prevents changes in concentration of the reagent either due to evaporation or crystallisation. The heater 52 is provided with a thermostat 54 which can be controlled to within ±0.1° C. The downstream end of the nickel tube is arranged to cause fluid which it contains to enter a cuvette 55 of a spectrophotometer 56 which also includes a lamp (not shown) housed in a housing 57. Material passing through the covette is subjected to spectrophotometric analysis. Each of the analytical modules functions in the way described in European Patent Specification No, 0047130. Each analytical module includes a cooling system for the electronic components which it contains; a single cooling duct can be provided in the main framework beneath each of the modules.

Figure 6:
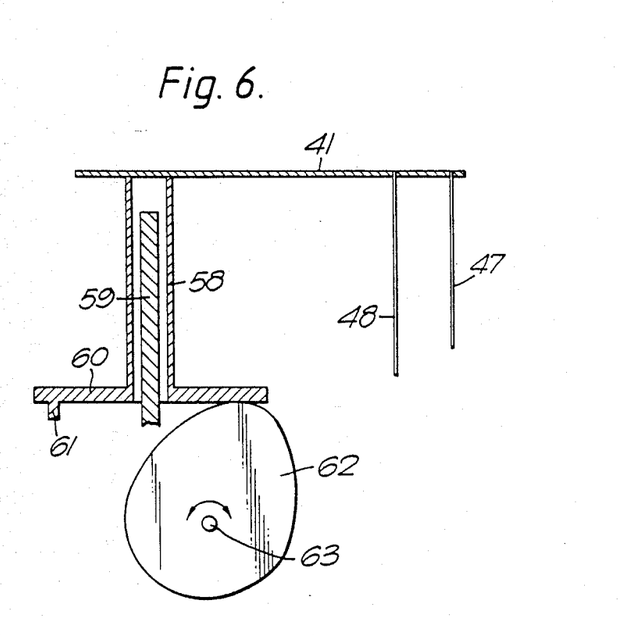
FIG. 6 is a schematic side elevational view of the probe-moving mechanism of the apparatus.
Figure 7:
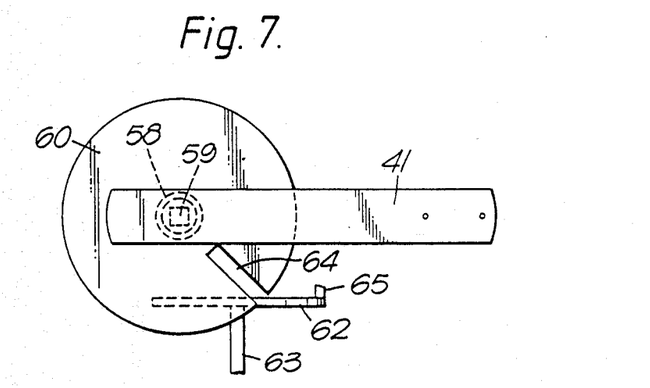
FIG. 7 is a schematic plan view of the mechanism shown in FIG. 6.

Each analytical module includes a mechanism for moving the probe-carrying arm 41. This mechanism is not shown in FIG. 5, but its operation is schematically illustrated in FIGS. 6 and 7. Arm 41 is fixed to a hollow, movable shaft 58 which is positioned loosely about a fixed vertical rod 59. The base of shaft 58 is secured to a circular disc 60 the lower surface of which carries a stop member 61. An eccentric cam 62, which is rotatable about a horizontal axis 63, contacts the underside of disc 60. In the position as shown in FIG. 6, cam 62 is holding disc 60, shaft 58 and arm 41 at a level close to their maximum upward travel. If the cam rotates in a clockwise sense from the position shown in FIG. 6, disc 60, shaft 58 and arm 41 will be lowered until the arm 41 rests on the top of rod 59. As shown in FIG. 7, disc 60 includes a radial slot 64 and cam 62 carries a pin 65. The pin and slot are arranged so that the pin engages with the slot when the cam has lifted parts 60, 58 and 41 to the maximum of their upward travel. Thus if the cam 62 is rotated counterclockwise from the position shown in FIG. 7, pin 65 will engage in slot 64 so that further rotation of the cam results in disc 60 being rotated in a clockwise sense as seen in FIG. 7. As cam 62 rotates even further, pin 65 once again comes free of slot 64, so that no further rotation of disc 60 occurs. The contact between the cam profile and disc 60, however, means that the parts 60, 58 and 41 will be lowered to a new position in which arm 41 is angularly displaced with respect to its initial position shown in FIG. 7. The stop member 61 cooperates with a fixed member (not shown) to ensure that the disc 60 does not overshoot the limit of its desired rotation once pin 65 leaves the radial slot 64. Reversal of the drive to shaft 63 will result in this sequence of movements being reversed. The degree of angular movement of arm 41 is such as to move the probes 47 and 48 from the first operative position in which probe 47 enters vial 5 and probe 48 enters one of the reagent containers 36, and the second operative position in which both of probes 47 and 48 enter one of the containers 37 of deionised water. The initial upward movement of arm 41 raises probes 47 and 48 out of vial 5 and receptacle 36, respectively; angular movement of the arm 41 then proceeds to carry the probes away from the vial 5 and receptacle 36 to a position above receptacle 37. The arm is then lowered, thus placing probes 47 and 48 into the deionised water in receptacle 37. Generally speaking, an angular rotation of 20° to 75° will be sufficient to achieve this result. The drive to cam 62 is provided by a stepping motor (not shown) which is under the control of a microprocessor (not shown). The use of a second stepping motor, instead of the same motor as that used to operate peristaltic pump 49, enables carefully controlled acceleration and decleration of the movement of arm 41, independently of operation of the pump 49, thus preventing splashing of sample or reagent.

Cam 62 also controls movement of the movable stop member 40 through a further mechanism (not shown) so that the member 40 is made to undergo an angular movement which is similar to that of, and takes place at the same time as that of, the arm 41.

Figure 9:
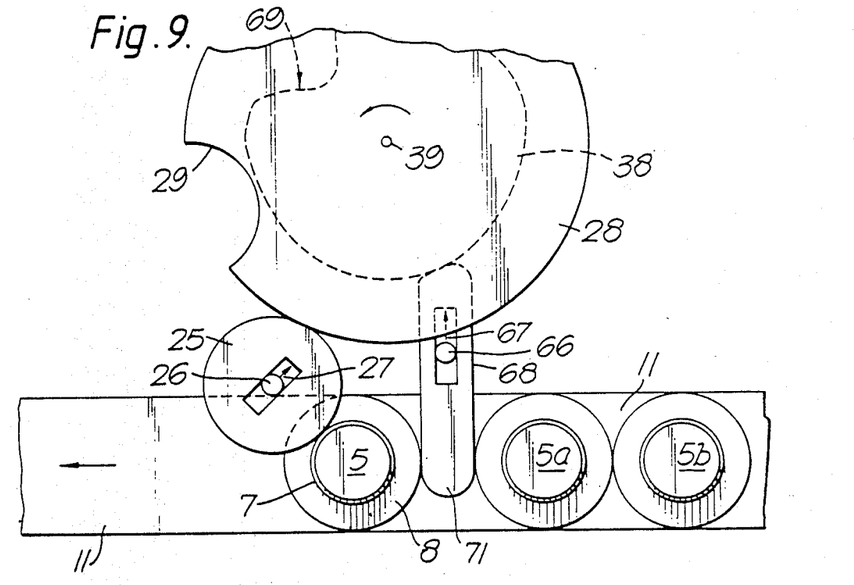
FIG. 9 is a schematic plan view of the entry gate of the apparatus.
Figure 10:
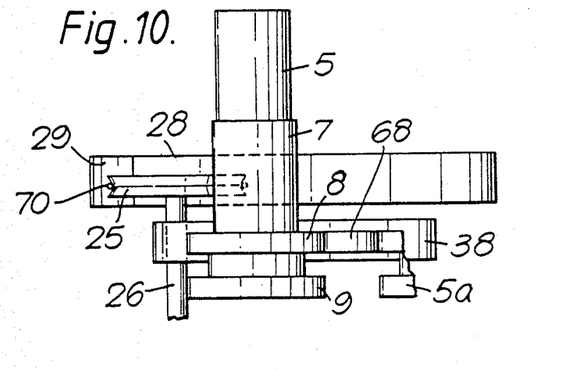
FIG. 10 is a schematic side elevational view of the mechanism shown in FIG. 9.

Referring now to FIGS. 9 and 10, the entry gate 2 comprises a wheel 25 which rotates about a spindle 26 which is biased in the direction of arrow 27. This urges the surface of wheel 25 against the profile of a generally circular cam 28. This cam includes an indented region 29 which engages with wheel 25 as a result of the biasing force acting along line 27. Beneath cam 28 is a further cam 38 carried on a common axis 39. Lower cam 38 also includes an indented region 69. A lever 68 fits over a spindle 66 and is urged in the direction of arrow 67 towards the profile of cam 38. As can be seen in FIG. 10, wheel 25 carries around its periphery a rubber ring 70. This ensures that rotation of cam 28 drives the wheel 25, and in turn that wheel 25 rotates the support cup 7 with which it is in contact as shown in FIG. 9. The entry gate shown in FIGS. 9 and 10 operates as follows. In the position shown in FIG. 9, one vial 5 is being held at the entry gate, and a succession of vials 5a, 5b etc. are held by lever 68 in a queue for admission to the gate itself. As cams 28 and 38 rotate about axis 39 in an anticlockwise direction, the indented surface 29 of cam 28 first meets the surface of wheel 25, which is urged into the depression 29 under the biasing action acting on spindle 26. This causes wheel 25 to move away from conveyor 11, thus freeing vial 5 to move towards the left as shown in FIG. 9 when the conveyor 11 is driven. Once the vial has moved away from the entry gate, the wheel 25 moves out of the indent 29 and thus once more closes the entry gate. Shortly after wheel 25 has emerged from depression 29, lever 68 makes contact with depression 69 on the surface of cam 38. The biasing force acting on lever 68 causes the rear end of the lever to enter depression 69, so that the front end 71 of lever 68 retracts from carriageway 11, thus allowing vial 5a to move to the left along the conveyor. When vial 5a passes the position of lever 68, it is retained by wheel 25. As the wheel comes into contact with vial 5a, lever 68 is pushed outwardly by the trailing surface portion of depression 69, and thus comes back across the path of conveyor 11 to hold vial 5b. The contact between the rubber ring 70 of wheel 25 and the upper part of support cup 7 causes the latter to rotate while it is held at the entry gate, and this in turn causes vial 5 carried by support cup 7 to rotate in a like manner. Thus bar code 6 (see FIG. 3) is rotated while the vial 5 is at the entry gate, thus permitting the reading device 3 to read the bar code label 6. The ratio between the diameters of wheel 25 and that part of the support cup 7 with which it is in contact is such that the latter rotates at least three times while it is held at the entry gate. This enables an unambiguous read-out of the bar code label 6 to be obtained.

Depending on the size of cams 28 and 38, there may be one or more recessed regions 29 and 69, respectively, in their circumferences. It is preferred, however, for the cams to have just one recessed region and for them to be rotated exactly once in the course of each vial admission cycle. The drive to cams 28 and 38 is through a motor (which may be a stepping motor under the control of a microprocessor) which has been omitted from the drawings for reason of clarity.

After a vial 5 has passed the entry gate 2, it moves along conveyor 11 to the first analysis station adjacent to module 4a, where it is stopped by movable stop member 40. The probe-carrying arm 41 then moves from the second operative position to the first operative position. Probe 47 then enters the open top of vial 5, while probe 48 enters the reagent receptacle 36a. Peristaltic pump 49 is then driven by stepping motor 50 for a predetermined time, thus aspirating reagent through probe 48 and sample through probe 47. When stepping motor 50 stops driving the pump 49, the mechanism shown in FIGS. 6 and 7 lifts arm 41 and then rotates it through a predetermined angular rotation whereupon it is lowered so that the probes 47 and 48 enter the container 37a of deionised water. Pump 49 is then started once again, so that deionised water is drawn into probes 47 and 48. Simultaneously, the sample and reagent which have already been drawn into tubes 51 after entry via probes 47 and 48 are combined at the Y-piece, and enter the coiled nickel tube 53 which is wound about heater 52. The peristaltic pump continues operating so that the deionised water pushes along the "active slug" of combined sample and reagent. When the active slug reaches cuvette 55, the pump 49 stops and the spectrophotometer 56 is operated to make a colorimetric analysis of the active slug. It will be appreciated that the measurement taken by the spectrophotometer can be conducted while the pump 49 is operating; the mode of operation selected will depend on the analytical test which is being performed. When this measurement has been taken, pump 49 operates so that the contents of tube 53 are evacuated to one of the waste containers 34 or 35. Thereafter, the drive to the cam mechanism of FIGS. 6 and 7 is reversed, so that probes 47 and 48 are lifted out of deionised water container 37a, and are moved back to their first operative position ready for receiving the next vial 5. As soon as the arm 41 has moved out of its first operative position to that where the probes 47 and 48 are immersed in the container of deionised water, the movable stop member 40 can undergo angular movement so as to release the restraint from the support cup holding vial 5. This enables the vial to move down towards the next analysis station adjacent to module 4b, and movement of all of the stop members 40 is arranged so that the next stop member is in its restraining position before vial 5 reaches module 4b. This sequence is repeated until all of the vials have passed through all of the analysis stations. When a vial has left the last of the analysis stations, it is carried by the continuous drive acting on conveyor 11 towards the curved exit guide 17. This directs the support cups with their vials away from conveyor 11 onto collection tray 18. An optical mechanism (not shown) is provided in the vicinity of exit guide 17 to ensure that no obstruction builds up downstream of the guide. This mechanism operates so that if the light beam is obstructed for more than a predetermined time, the drive to the conveyors and to the moving parts of the analytical modules is cut off. If the anti-fouling beam remains intercepted for a first, predetermined time, an audible alarm is sounded. If the beam remains intercepted after a further predetermined time, drive is cut off and the analysis apparatus effectively shuts down. The latter time is chosen so that vials subsequent to the one which is intercepting the anti-fouling beam will not have had time to reach back to the last of the analysis stations before the system is shut down. This ensures that, if shut-down is necessary, all of the samples which have passed the last of the movable stop members 40 will have completed their full sequence of analyses.

The microprocessor (not shown) used to control the operating sequence described above ensures that the stepping motor 50 is accurately indexed so that each analysis operation commences with the motor 50 at exactly the same position in its cycle.

When all of the vials supplied for analysis have completed their course through all of the analytical stations, the microprocessor is arranged to effect small, regular rotations of the pump 49 so as to prevent deformation of the pump tubes due to the compressive action of the pump rollers being applied to the same portion of pump tubing for a length of time.

By employing different reagents for each of the modules 4a, 4b etc., it is possible by means of the present apparatus, to carry out a large number of analytical tests on each of a series of samples. The analysis rate can be high, and the provision of a bar code label on each of the vials ensures that sample identity is carefully preserved. The operation of entry gate 2, bar code reader 3, movable stop member 40 and arm 41 is controlled by suitable synchronising means, for example a microprocessor. The same microprocessor can advantageously read and store the result of the analysis carried out within each of the modular analysis units and co-ordinate the results with the sample identity codes read by the device 3.

It will not always be necessary to carry out all of the possible analytical tests on every one of the samples in the course of a given run. The bar code labels 6 may include, as well as a sample identity code, instructions as to which of the tests are to be carried out on that sample. This enables the microprocessor to passivate the operating sequence of selected analysis modules in response to the bar codes.

The apparatus of the present invention is particularly beneficial in carrying out clinical analyses of samples such as blood serum. The apparatus will also find use in non-clincial analysis, e.g. in the analysis of agricultural, pharmaceutical and industrial samples.

What is claimed is:

1. Automatic analysis apparatus, comprising:
   a first endless conveyor;
   a second endless conveyor being disposed in a side by side relationship with said first endless conveyor; such that respective longitudinal side edges of said first and second endless conveyors are adjacent to one another;
   means for driving said first and second endless conveyors continuously and in first and second respectively opposite directions during operation of the apparatus;
   means for transferring a sample vial from said second endless conveyor to said first endless conveyor;
   an entry gate disposed along said first endless conveyor, for retaining sample vials carried by the first endless conveyor and selectively admitting sample vials to the first endless conveyor downstream of the entry gate;
   a plurality of analytical modules disposed adjacent to said first endless conveyor, downstream of said entry gate, each of said analytical modules comprising:
      a moveable stop member for retaining a sample vial on the conveyor in a position adjacent to the module; a sample probe for removing sample from a vial retained by the stop member;
      means for moving the sample probe between a first operative position in which the probe may be inserted into a vial held by said stop member to remove sample therefrom and a second operative position in which the sample probe is clear of the vial;
      means for processing a sample removed by the sample probe; and
      means for controlling the movement of the stop member to enable it to retain a sample vial to allow a sample to be removed therefrom and to release the vial when the sample has been removed therefrom;
   identification means adjacent said entry gate for reading an identifying code carried by a sample vial; and
   synchronizing means for controlling the operation of the entry gate, the identification means, the means for moving the sample probe and the means for controlling the stop member, wherein the synchronizing means and the identification means are arranged so that information carried by a vial can be processed to determine the modules to which the vial is to be directed, thereby allowing selective testing of the sample in the vial.

2. The apparatus of claim 1, wherein said synchronizing means comprises a microprocessor programmed to coordinate the operation of said entry gate, said identification means, said means for moving the sample probe and said means for controlling the movement of the stop number.

3. The apparatus of claim 1, wherein the entry gate comprises:
   a first, generally horizontal cam having a generally circular profile except for a single indented region;
   a generally horizontal wheel urged against the first cam, having a radius substantially smaller than that of the cam, acting as a cam follower, said wheel extending across the first endless conveyor to prevent the passage of a vial when the wheel is in contact with the non-indented region of the cam, and permitting passage of a vial when in contact with the indented region of the cam;
   a second cam having an indented profile; and
   a retractable member cooperating with said second cam, extending across the first endless conveyor to prevent passage of the vials except when the retractable member contacts an indented area of the second cam, said second cam being arranged to operate out of phase with respect to said first cam so that at least one of the generally horizontal wheel and the retractable member is positioned across the first endless coveyor during the operation of the apparatus.

4. The automatic analysis apparatus defined in claim 1 wherein each of the analytical modules further comprises a reagent container adjacent to said conveyor means and a reagent probe for extracting a quantity of reagent from said reagent container, said probe moving means acting on said reagent probe as well as on said sample probe.

5. The automatic analysis apparatus as defined in claim 4 wherein each of said analytical modules includes means for supplying a reagent to said reagent container in said analytical module and further comprises a container for a carrier liquid, said carrier liquid container being in communication with said analytical module, said sample probe being located in said carrier liquid container when in said second operative position.

6. Apparatus as claimed in claim 5, wherein the means for moving the sample and reagent probes is arranged so that, in said second operative position, the reagent probe is located in the container for a carrier liquid.

7. Apparatus as claimed in claim 6, wherein said means for moving the sample and reagent probes consists of a hollow moveable shaft having a disc at its base, the hollow shaft being secured to said arm and being positioned loosely over a fixed vertical rode, and a cam rotateable about a generally horizontal axis and positioned so as to cooperate with said disc in a manner such that rotation of the cam acts upon the disc and hence upon said arm to raise and lower the probes carried by said arm.

8. Apparatus as claimed in claim 7, wherein said disc is provided with a radial slot and wherein said cam is provided with a pin for cooperating with the radial slot so that, during a predetermined portion of the rotation of the cam, said pin can enter said radial slot and thereby cause said disc to rotate with respect to said fixed vertical rod, thereby causing similar rotation of the arm and the probes carried thereby.

9. Apparatus as claimed in claim 8, wherein the cam with its pin and the disc with its radial slot are arranged such that the cam can cause rotation of the disc through an angle in the range of from 20° to 75°.

10. Apparatus as claimed in claim 8, which further comprises a stepping motor arranged to drive said cam, and wherein said cam is arranged to control the movable stop member between the holding position, in which it holds a vial in a stationary position on first endless conveyor to a further position where the vial is free to be moved by the first endless conveyor.

11. The automatic analysis apparatus as defined in claim 4, wherein each of said analytical modules includes an arm which carries said sample probe and said reagent probe.

12. The automatic analysis apparatus as defined in claim 4 wherein each of said analytical modules additionally includes a peristaltic pump for extraction of sample and reagent through said sample and reagent probes, respectively, and wherein said synchronizing means is arranged to control the operation of each of said peristaltic pumps.

13. The apparatus of claim 1, wherein said means for transferring comprises a guide member arranged so that vials travelling along said second endless conveyor come into contact with said guide member and are transferred to the first endless conveyor.

14. The automatic analysis apparatus as defined in claim 13, wherein said guide member is a curved guide located substantially near one end of said endless conveyors and wherein, in the vicinity of said curved guide, there is a narrow intermediate supporting surface positioned between said two endless conveyors, said supporting surface having positioned thereon an upstanding wall which is inclined at an acute angle with respect to the direction of movement of the two endless conveyors, and wherein said wall has a wedge-shaped cross-section at its end adjacent to said curved guide.

* * * * *